(12) United States Patent
Kostrzewski

(10) Patent No.: US 8,631,993 B2
(45) Date of Patent: *Jan. 21, 2014

(54) SURGICAL INSTRUMENT WITH DOUBLE CARTRIDGE AND ANVIL ASSEMBLIES

(75) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/602,176

(22) Filed: Sep. 2, 2012

(65) Prior Publication Data

US 2012/0325892 A1 Dec. 27, 2012

Related U.S. Application Data (63) Continuation of application No. 12/783,994, filed on May 20, 2010, now Pat. No. 8,276,802.

(60) Provisional application No. 61/224,854, filed on Jul. 11, 2009.

(51) Int. Cl.
*A61B 17/10* (2006.01)
*A61B 17/04* (2006.01)

(52) U.S. Cl.
USPC ................................... 227/179.1; 227/180.1

(58) Field of Classification Search
USPC ............... 227/175.1–182.1, 19; 606/219, 221
See application file for complete search history.

(56) References Cited

U.S. PATENT DOCUMENTS

| | | | | |
|---|---|---|---|---|
| 3,867,944 | A * | 2/1975 | Samuels | 606/158 |
| 4,505,414 | A * | 3/1985 | Filipi | 227/19 |
| 4,773,420 | A * | 9/1988 | Green | 227/178.1 |
| 4,930,674 | A * | 6/1990 | Barak | 227/179.1 |
| 5,188,636 | A * | 2/1993 | Fedotov | 606/144 |
| 5,662,260 | A | 9/1997 | Yoon | |
| 6,673,088 | B1 * | 1/2004 | Vargas et al. | 606/185 |
| 7,237,708 | B1 | 7/2007 | Guy et al. | |
| 8,262,676 | B2 * | 9/2012 | Ewers et al. | 606/139 |
| 8,276,802 | B2 * | 10/2012 | Kostrzewski | 227/179.1 |
| 2007/0034668 | A1 * | 2/2007 | Holsten et al. | 227/179.1 |
| 2009/0005808 | A1 * | 1/2009 | Hess et al. | 606/219 |
| 2009/0132021 | A1 | 5/2009 | Shifrin et al. | |
| 2009/0302092 | A1 | 12/2009 | Kasvikis et al. | |
| 2010/0065606 | A1 * | 3/2010 | Stopek | 227/176.1 |
| 2010/0301098 | A1 * | 12/2010 | Kostrzewski | 227/179.1 |
| 2011/0087279 | A1 * | 4/2011 | Shah et al. | 606/219 |

FOREIGN PATENT DOCUMENTS

WO  WO 2006/082586 A2  8/2006
WO  WO 2008/081210 A1  7/2008

OTHER PUBLICATIONS

European Search Report for EP 10251239.9-2310 date of completion is Oct. 11, 2010 (6 pages).

* cited by examiner

*Primary Examiner* — Robert Long

(57) ABSTRACT

An end effector for use with a surgical instrument having a first cartridge assembly configured to deploy a first set of fasteners and a second cartridge assembly disposed distally of the first cartridge assembly. The second cartridge assembly is configured to move between an open position and an approximated position relative to clamp tissue. A central rod extends between the first cartridge assembly and the second cartridge assembly.

25 Claims, 11 Drawing Sheets

SURGICAL INSTRUMENT WITH DOUBLE CARTRIDGE AND ANVIL ASSEMBLIES

This application is a continuation of U.S. patent application Ser. No. 12/783,994, filed May 20, 2010, now U.S. Pat. No. 8,276,802 which claims priority from provisional application serial no. 61/224,854, filed Jul. 11, 2009, the entire contents of each of these applications are incorporated herein by reference.

BACKGROUND

1. Technical Field

The present disclosure relates generally to surgical instruments and methods for performing surgery. More specifically, the present disclosure relates to surgical instruments and methods for clamping, cutting, and/or joining tissue.

2. Background of Related Art

Certain surgical stapling instruments are used for applying rows of staples through compressed living tissue. These surgical stapling instruments are employed, for example, for fastening tissue or organs prior to transaction or resection or during anastomoses. In some cases, these surgical stapling instruments are utilized for occluding organs in thoracic and abdominal procedures.

Typically, such surgical stapling instruments include an anvil assembly, a cartridge assembly for supporting an array of surgical staples, an approximation mechanism for approximating the cartridge and anvil assemblies, and a firing mechanism for ejecting the surgical staples from the cartridge assembly.

In use, a surgeon initially approximates the anvil and cartridge assemblies. Next, the surgeon can fire the instrument to place staples in tissue. Optionally, the surgeon may use the same instrument or a separate device to cut the tissue adjacent or between the row(s) of staples.

SUMMARY

The present disclosure relates in one aspect to an end effector for use with a surgical instrument. The end effector includes a first cartridge assembly configured to deploy a first set of fasteners and a second cartridge assembly disposed distally of the first cartridge assembly. The second cartridge assembly is configured to move between an open position and an approximated position. A central rod extends between the first cartridge assembly and the second cartridge assembly.

The end effector preferably also includes a first anvil assembly disposed distally of the first cartridge assembly and a second anvil assembly disposed distally of the first anvil assembly.

Preferably, each of the first anvil assembly and second anvil assembly is mounted on the central rod for movement in response to movement of the central rod. The second cartridge assembly preferably includes a second set of fasteners and a fastener pusher adapted to move between a distal position and a proximal position to eject the second set of fasteners from the second cartridge.

In some embodiments, the second cartridge assembly includes a biasing member, biasing a cartridge housing against the fastener pusher. The first cartridge assembly can include a knife movable between a proximal position and a distal position.

In some embodiments, the end effector is removably mountable to a surgical instrument.

In some embodiments, the first anvil assembly includes a plurality of anvil pockets arranged in a substantially annular array and configured to deform the first set of fasteners arranged in a substantially annular array.

In another aspect, the present disclosure relates to a surgical instrument including a handle assembly and an elongated portion extending distally from the handle assembly. The elongated portion has a proximal portion and a distal portion. The surgical instrument further includes an end effector disposed adjacent the distal portion of the elongated portion. The end effector includes a first cartridge assembly configured to deploy a first set of fasteners, a first anvil assembly disposed distally of the first cartridge assembly, a second anvil assembly disposed distally of the first anvil assembly, and a second cartridge assembly disposed distally of the second anvil assembly. The second cartridge assembly is configured to move between an open position and an approximated position relative to the second anvil assembly. A central rod extends between the first cartridge assembly and the second cartridge assembly.

In some embodiments, the second cartridge assembly is configured to deploy a second set of fasteners once the second cartridge assembly has moved to the approximated position and includes a fastener pusher adapted to move between a distal position and a proximal position to eject the second set of fasteners. Preferably, each of the first anvil assembly and the second anvil assembly is mounted on the central rod for movement in response to movement of the central rod.

The first cartridge assembly may further include a knife movable between a proximal position and a distal position. The first and second sets of fasteners can be arranged in a substantially annular array.

The present disclosure relates in another aspect to a method for performing surgery. This method includes the steps of: (a) inserting an end effector inside a tubular organ, the end effector including a first cartridge assembly housing a first set of fasteners, a first anvil assembly disposed distally of the first cartridge assembly, a second anvil assembly disposed distally of the first anvil assembly, a second cartridge assembly disposed distally of the second anvil assembly, and configured to move between an open position and an approximated position relative to the second anvil assembly, and a central rod extending between the first cartridge assembly and the second cartridge assembly; (b) drawing a first tissue portion of the tubular organ toward the central rod and into a first area located between the second cartridge assembly and the second anvil assembly; (c) drawing a second tissue portion of the tubular organ toward the central rod and into a second area located between the first anvil assembly and the second anvil assembly; (d) drawing a third tissue portion of the tubular organ toward the central rod and into a third area located between the first anvil assembly and the first cartridge assembly; and (e) firing the end effector to fasten together sections of the first tissue portion and to fasten sections of the third tissue portion.

DETAILED DESCRIPTION OF THE EMBODIMENTS

Embodiments of the presently disclosed surgical instrument are described in detail with reference to the drawings, wherein like reference numerals designate corresponding elements in each of the several views. In the description that follows, the term "proximal" refers to the end or portion of the surgical instrument closer to the user, whereas the term "distal" refers to the end or portion of the surgical instrument further away from the user.

Figures 1, 2:
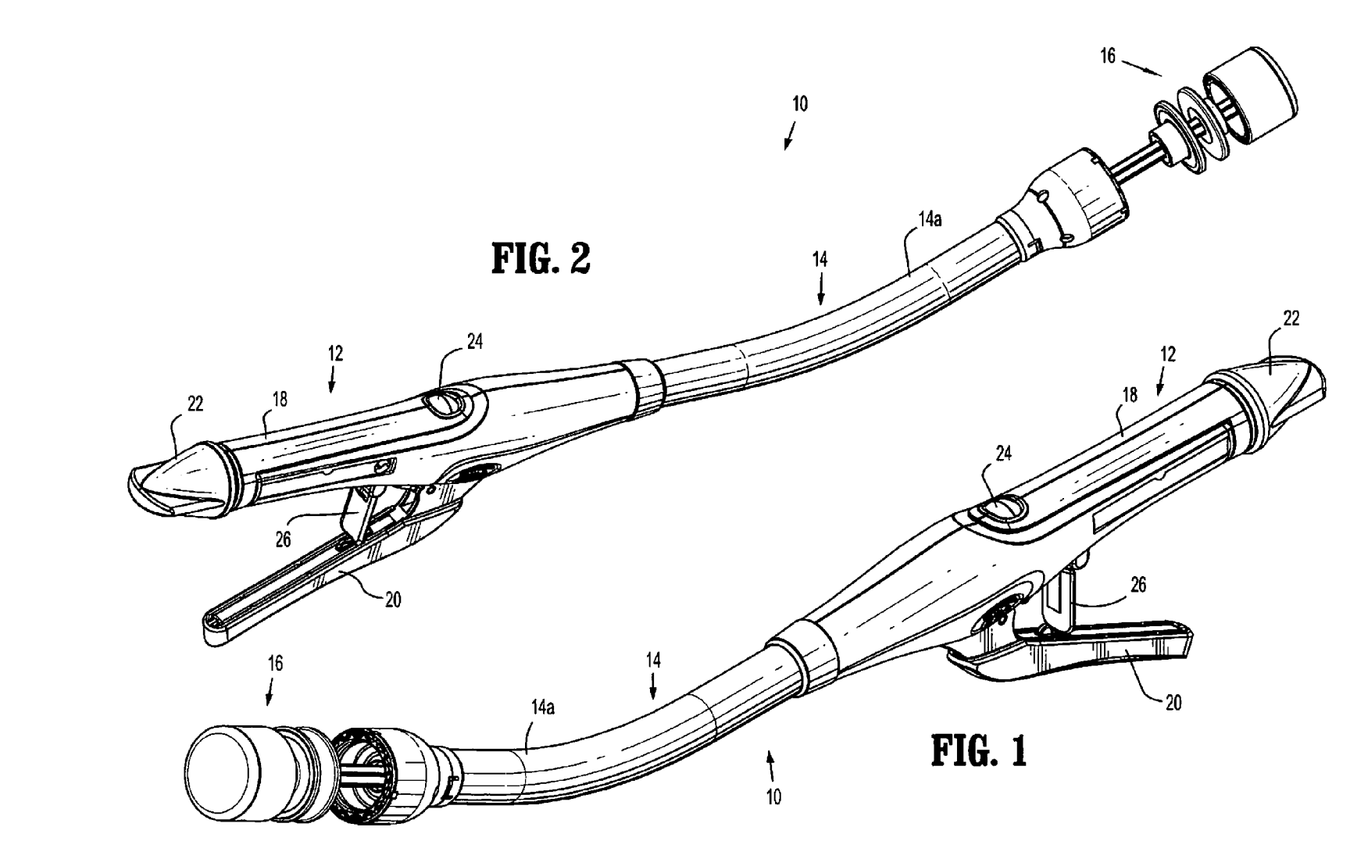
FIG. 1 is a front perspective view of a surgical instrument according to an embodiment of the present disclosure.
FIG. 2 is a rear perspective view of the surgical instrument shown in FIG. 1.

FIGS. 1 and 2 illustrate an embodiment of the presently disclosed surgical instrument 10. In the interest of brevity, the present disclosure focuses on end effectors for the disclosed surgical instrument. U.S. Pat. No. 7,303,106, the entire contents of which are incorporated herein by reference, describes in detail the structure and operation of an embodiment of surgical instrument 10. In general, surgical instrument 10 includes a handle assembly 12, an elongated central body portion 14 including a curved elongated outer tube 14a, and an end effector or distal end (head) portion 16. Elongated central body portion 14 extends distally from handle assembly 12 and operatively couples end effector 16 to handle assembly 12. In operation, end effector 16 is approximated to clamp tissue upon actuation of an approximation knob and fires fasteners and advances a cutting device upon actuation of handle assembly 12.

Handle assembly 12 includes a stationary handle 18, a pivotable firing trigger 20, a rotatable approximation knob 22 and an indicator 24. In certain embodiments, stationary handle 18 is made of a thermoplastic, such as polycarbonate. In other embodiments, stationary handle 18 is formed of an elastomeric material. Stationary handle 18 may nevertheless be formed of any suitable material. In some embodiments, stationary handle 18 has a hollow body that houses internal components of handle assembly 12. U.S. Pat. No. 7,303,106, the entire contents of which have previously been incorporated by reference, describes in detail the internal components of handle assembly 12.

Handle assembly 12 further includes a trigger lock 26 for preventing or at least minimizing the risk of inadvertently firing surgical instrument 10 (e.g., prior to approximation of various portions of the end effector). In the embodiment depicted in FIGS. 1 and 2, trigger lock 26 is pivotally mounted to stationary handle 18. During use, trigger lock 26 is configured to move relative to stationary handle 18 between a locked position and an unlocked position. In the locked position, trigger lock 26 engages firing trigger 20 and precludes, or at least hinders, movement of firing trigger 20 with respect to stationary handle 18. In the unlocked position, trigger 26 allows firing trigger 20 to move or pivot relative to stationary handle 18. Stationary handle 18 additionally includes an indicator 24 to indicate to a user whether end effector 16 is approximated and is ready to be fired, for example. Indicator 24 may include a bulbous or convex shape extending outwardly from a top surface of stationary handle 18.

Figure 3:
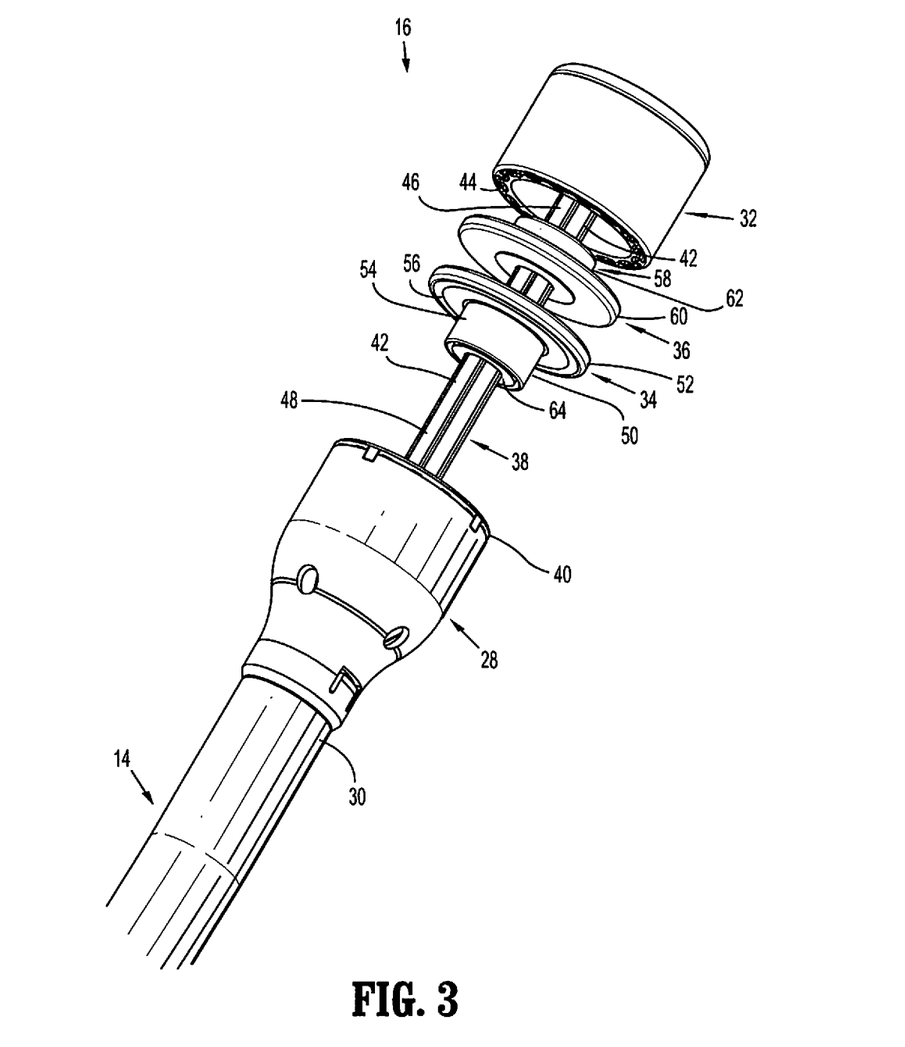
FIG. 3 is a perspective view of a distal portion of the surgical instrument shown in FIGS. 1 and 2.

As seen in FIG. 3, end effector 16 includes a first proximal cartridge assembly 28 positioned at a distal end 30 of elongated central body portion 14, a second distal cartridge assembly 32 positioned at a more distal location, a first anvil assembly 34, a second anvil assembly 36 positioned distal of the first anvil assembly 34, and a central rod 38 extending distally from first cartridge assembly 28 to second cartridge assembly 32. First and second cartridge assemblies 28, 32 are both configured to deploy or eject fasteners 78, 80 (FIG. 6), such as staples. In certain embodiments, first and second cartridge assemblies 28, 32 include one or more substantially annular rows of slots 44 each adapted to retain one or more fasteners (FIG. 6) likewise arranged in substantially annular rows. Although the drawings show second cartridge assembly 32 (and first cartridge 28) with substantially annular rows of slots 44, the slots of the cartridges may have other configurations.

With continued reference to FIG. 3, central rod 38 operatively interconnects first cartridge assembly 28, first anvil assembly 34, second anvil assembly 36, and second cartridge assembly 32. In some embodiments, central rod 38 protrudes about 2 to about 3 inches beyond a distal end 40 of first cartridge assembly 28. In the illustrated embodiments, central rod 38 includes one or more longitudinal keys 42 along its length. Longitudinal keys 42 are configured to maintain the orientation of first and second anvil assemblies 34, 36 with respect to center rod 38 as first and second anvil assemblies 34, 36 each include key slots (not shown) adapted to engage longitudinal keys 42 of central rod 38. The engagement of longitudinal keys 42 of central rod 38 and key slots (not shown) of first and second anvil assemblies 34, 36 assist in preventing rotation of first and second anvil assemblies 34, 36 relative to central rod 38 to maintain alignment of the anvil pockets of the anvil assemblies 34, 36 with the staples. When end effector 16 is fully assembled, second cartridge assembly 32 is mounted on a distal end 46 of central rod 38.

In addition, after end effector 16 has been fully assembled (either by the user or alternatively in manufacture and shipped and packaged assembled), first anvil assembly 34 is positioned proximally relative to second anvil assembly 36. First anvil assembly 34 includes a tubular portion 50 and disk 52 adjacent a distal end 54 of tubular portion 50. Tubular portion 50 defines a longitudinal opening 64 extending therethrough. Longitudinal opening 64 is configured to accommodate central rod 38. Anvil assembly 34 is slidably positioned on central rod 38. It is contemplated that tubular portion 50 may be made of a polymer, such as a plastic, or any other suitable material. Disk 52 may be formed of a metal, such as stainless steel, or any other suitable material. Disk 52 includes one or more anvil pockets or concavities 66 (FIG. 6) disposed on a proximal surface 56 thereof and thus face in a proximal direction. Pockets 66 are adapted to deform fasteners 78 (FIG. 6) ejected in a distal direction from first cartridge assembly 28 into contact with the pockets. In some embodiments, pockets 66 (FIG. 6) of disk 52 are arranged in substantially annular rows. Regardless of the specific arrangement, pockets 66 (FIG. 6) of disk 52 are substantially aligned with slots 68 (FIG. 6) of first cartridge assembly 28. This substantial alignment between pockets 66 (FIG. 6) of disk 52 and slots 68 of first cartridge assembly 28 facilitates proper deformation of fasteners 78 (FIG. 6) deployed from first cartridge assembly 28 during the firing process.

Figure 6:
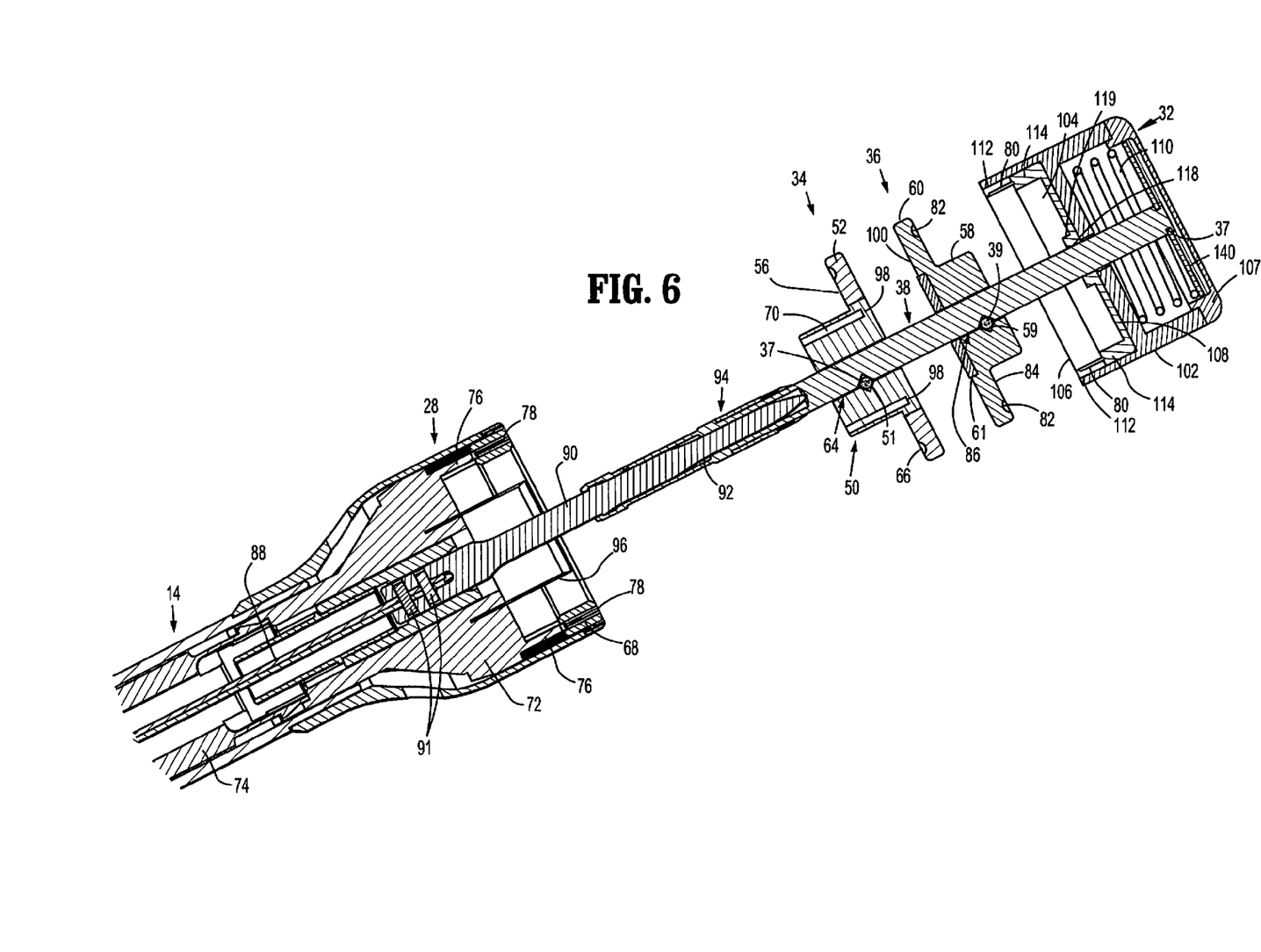
FIG. 6 is a longitudinal cross-sectional view of the distal portion of the surgical instrument shown in FIG. 1, taken around section 6 of FIG. 4.

As seen in FIGS. 3 and 6, second anvil assembly 36 is located distally with respect to first anvil assembly 34 when end effector 16 is fully assembled. Second anvil assembly 36 includes a tubular portion 58 and a disk 60 adjacent a proximal end 62 of tubular portion 58. Tubular portion 58 defines a longitudinal opening 86 (FIG. 6) extending therethrough. Longitudinal opening 86 of tubular portion 58 is configured to receive central rod 38. Anvil assembly 36 is slidably positioned on central rod 38. Moreover, tubular portion 58 may be made of a polymer, such as plastic, or any other suitable material. Disk 60 may be formed of a metal, such as stainless steel, or any other suitable material. Disk 60 includes one or more anvil pockets or concavities 82 (FIG. 6) arranged on a distal surface (facing in a distal direction) adapted to deform fasteners 80 (FIG. 6) ejected from second cartridge assembly 32 in a proximal direction into contact with the pockets 82 during the firing process. Pockets 82 may be arranged in substantially annular rows on the distal surface 84 (FIG. 6) of disk 60. Regardless of the specific arrangement, pockets 82 (FIG. 6) of disk 60 are substantially aligned with slots 112 (FIG. 6) of second cartridge assembly 32. This substantial alignment between pockets 82 (FIG. 6) of disk 60 and slots 112 of second cartridge assembly 32 facilitates proper deformation of fasteners 80 (FIG. 6). Disk 60 includes a cutting ring 61 on a proximal side.

As noted above, anvil assemblies 34 and 36 are slidably mounted on central rod 38. A detent mechanism can be provided to retain the anvil assemblies 34, 36 in an initial position. As shown, detent 59 on an inner surface of tubular portion 58 of anvil assembly 36 engages a groove 39 formed in central rod 38. A detent 51 on an inner surface of tubular portion 50 of anvil assembly 34 engages a groove 37 formed in central rod 38. In this manner, anvil assemblies 34 and 36 are held in position on the central rod 38 until the instrument is approximated to clamp tissue as described below.

Figure 4:
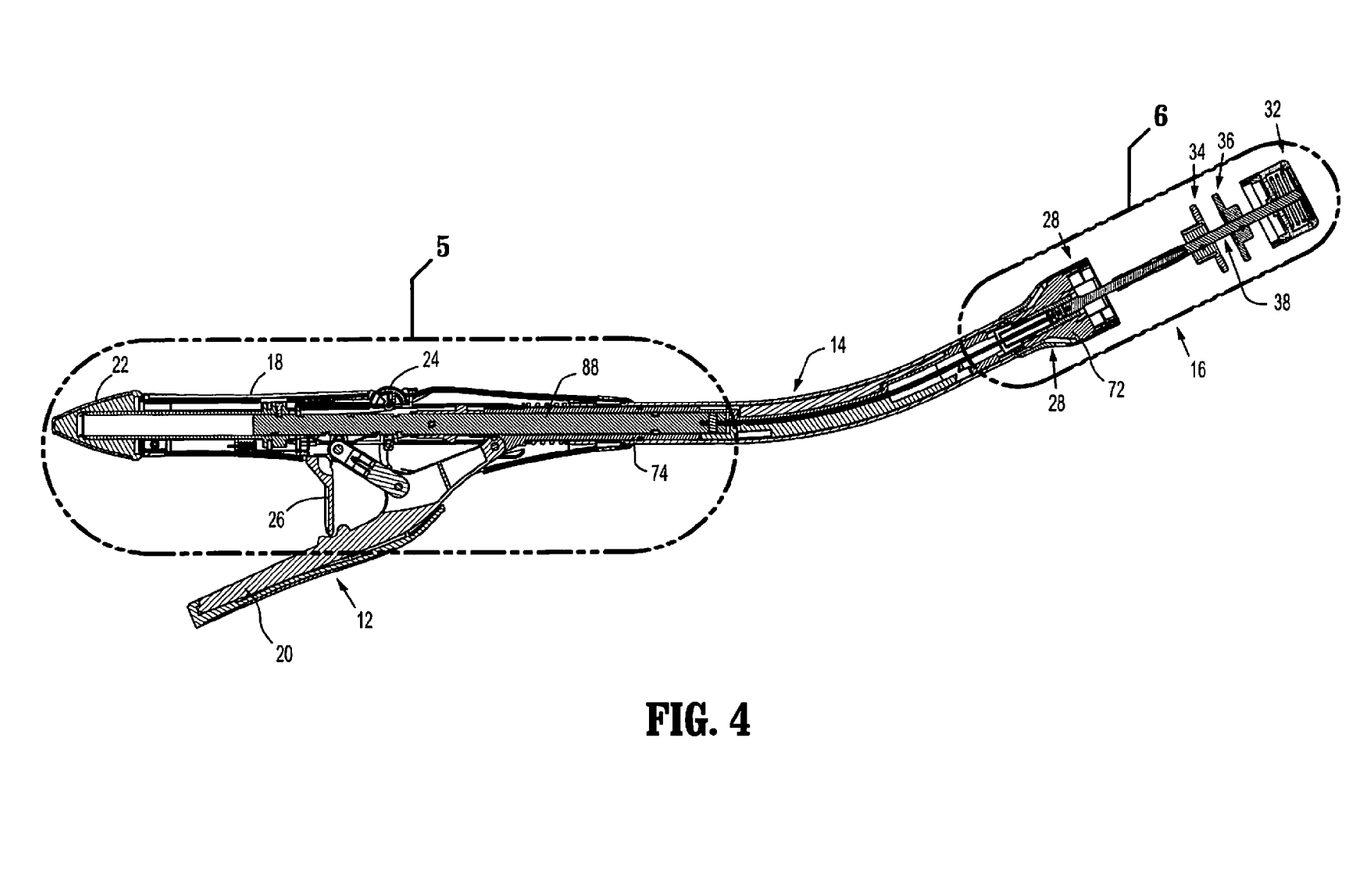
FIG. 4 is a longitudinal cross-sectional view of the surgical instrument shown in FIGS. 1-3.
Figure 5:
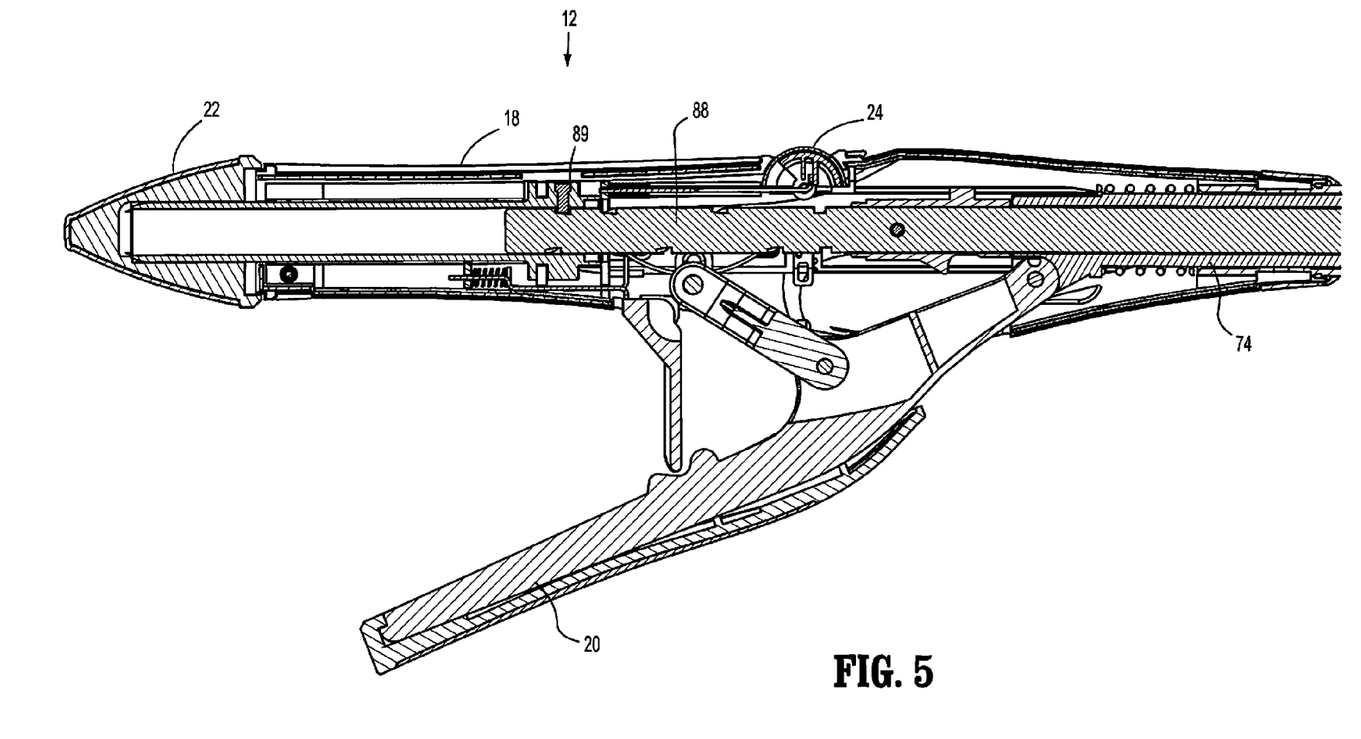
FIG. 5 is a longitudinal cross-sectional view of a handle assembly of the surgical instrument shown in FIG. 1, taken around section 5 of FIG. 4.

With reference to FIGS. 4 and 5, firing trigger 20 is operatively coupled to a fastener pusher 72 positioned inside first cartridge assembly 28. Surgical instrument 10 includes a firing link assembly 74 operatively interconnecting firing trigger 20 and fastener pusher 72. Firing link assembly 74 extends from handle assembly 12 to first cartridge assembly 28. In operation, actuation of firing trigger 20 causes a distal translation of firing link assembly 74 which causes a distal translation of fastener pusher 72. Fastener pusher 72 includes one or more fingers 76 (FIG. 6) dimensioned to be received in slots 68 of first cartridge assembly 28. When fastener pusher 72 moves distally in response to an actuation of firing trigger 20 (due to distal movement of firing link assembly 74), fingers 76 move distally toward slots 68 and urge fasteners 78 distally toward and into contact with first anvil assembly 34.

With continued reference to FIGS. 4-6, surgical instrument 10 further includes an approximation link assembly 88 operatively coupling approximation knob 22 to central rod 38. Rotation of knob 22 rotates an internal screw which is operatively connected to link assembly 88 via pin 89 to thereby move link assembly 88 in a proximal or distal direction, depending on the direction of rotation of knob 22.

As seen in FIG. 6, approximation link assembly 88 includes a rod 90 protruding distally from first cartridge assembly 28, which can optionally have a trocar tip as shown. Rod 90 can be pinned at a proximal region to approximation link assembly 88 via pins 91. Rod or shaft 90 is disposed in mechanical cooperation with central rod 38 (e.g., in a friction-fit relationship). Central rod 38 defines a longitudinal opening 92 dimensioned to receive rod 90. Longitudinal opening 92 extends through a proximal portion 94 of central rod 38. In operation, a rotation of approximation knob 22 effects a translation of approximation link assembly 88. As approximation link assembly 88 translates, connected rod 90 moves proximally or distally therewith. Since rod 90 is coupled to central rod 38, movement of rod 90 causes central rod 38 to move as well. While central rod 38 moves, second cartridge assembly correspondingly 32 moves in a distal or proximal direction. A user therefore may approximate second cartridge assembly 32 by rotating approximation knob 22 in a first direction (e.g., clockwise). In response to rotation of knob 22 in a first direction, approximation link assembly 88 moves proximally and moves rod 90 in a proximal direction. As rod 90 moves proximally, central rod 38 translates proximally and pulls second cartridge assembly 32 toward second anvil assembly 36 from an open position (e.g. FIG. 6) to an approximated position (e.g. FIG. 9), as described in detail below.

As shown in FIG. 6, first cartridge assembly 28 further includes a knife blade 96, or any suitable cutting device, movable between a retracted or proximal position and a deployed or distal position. Knife 96 is operatively connected to fastener pusher 72 and may have an annular configuration or shape. In some embodiments, knife 96 is made of a metal, such as stainless steel. In the retracted position, knife 96 is positioned within first cartridge assembly 28. In the deployed position, knife 96 is at least partially positioned outside of first cartridge assembly 28 to sever tissue. While knife 96 moves between the retracted and deployed positions, at least a portion of knife 96 passes through an annular space 70 defined in first anvil assembly 34 and through a breakable annular portion 98, as discussed below.

With continued reference to FIG. 6, first anvil assembly 34 is positioned on central rod 38 and includes annular space 70 defined in tubular portion 50. Annular space 70 surrounds longitudinal opening 64 and is dimensioned to receive knife 96. During use, annular space 70 guides the translation of knife 96 through first anvil assembly 34. First anvil assembly 34 also includes a breakable or weakened annular portion 98 substantially axially aligned with annular space 70. Breakable annular portion 98 may be made of ceramic, plastic, or any other suitable material and is positioned distally relative to annular space 70. Breakable annular portion 98 is made of a material that can be broken by knife 96 during the firing process. As knife 96 moves from the retracted position to the deployed position, knife 96 passes through annular space 70 of first anvil assembly 34 and then breaks breakable annular portion 98 of first anvil assembly 34. After knife 96 breaks through breakable annular portion 98, knife 96 continues moving toward second anvil assembly 36. The outer portion of the anvil 34 broken off by the knife can pass through the body or otherwise captured and retrieved.

As depicted in FIG. 6, second anvil assembly 36 is positioned on central rod 38 and includes tubular portion 58 having a proximal surface 100. Proximal surface 100 of tubular portion 58 serves as a knife cutting target. As such, proximal surface 100 of tubular portion 58 receives knife 96 and stops further distal translation of knife 96 during the firing process. It is made of a suitable material which enables the knife to become embedded therein to stop distal advancement or alternately, as shown in FIG. 6, includes a cut ring 61 positioned in the proximal surface into which the knife becomes embedded to limit movement of the knife.

With continued reference to FIG. 6, second cartridge assembly 32 includes a housing 102 for storing fasteners 80. Housing 102 defines an inner cavity 104 and a proximal aperture 106 dimensioned to receive at least a portion of tubular portion 58 of second anvil assembly 36 and central rod 38. Second cartridge assembly 32 also includes one or more slots 112 for retaining fasteners 80, a fastener pusher 108 disposed in inner cavity 104 and a biasing member 110 (such as a spring) operatively coupled between housing 102 and center rod retainer ring 140. In some embodiments, slots 112 are arranged in substantially annular rows. Irrespective of their arrangement, slots 112 are substantially axially aligned with distally facing pockets 82 of second anvil assembly 36 to facilitate proper deformation of fasteners 80 during the firing process. Fastener pusher 108 includes one or more fingers 114 adapted to urge fasteners 80 proximally toward second anvil assembly 36. Fingers 114 are configured to be received in slots 112 and extend in a proximal direction. Biasing member 110, which can be in the form of a spring for example, allows the fastener pusher 108 to move proximally independently from the cartridge housing 102 while second cartridge 32 is abutting compressed tissue.

As depicted in FIG. 6, fastener pusher 108 includes a tubular portion 119 defining a longitudinal lumen 118. Longitudinal lumen 118 is configured to receive a distal end 46 (FIG. 3) of central rod 38 and configured for permanent attachment to center rod 38.

A retainer ring 140 rests in groove 37 of center rod 38. Cartridge housing 102 of second cartridge 32 is biased by member 110 against a distal surface of fastener pusher 108. Biasing member 110 secures initial positioning relation of fasteners 80 and fastener pusher 108 to second cartridge 32 prior to clamping. Cartridge housing 102 includes housing cap 107 to prevent exposure of biasing member 110 and retainer ring 140 to body fluids and tissue.

FIGS. 7-14 illustrate the operation of surgical instrument 10. As discussed above, a clinician may use surgical instrument 10 to perform numerous surgical procedures. For example, surgical instrument 10 can be utilized to conduct a lower anterior resection. In any case, the clinician may employ surgical instrument 10 to clamp, cut, and/or join tissue. Before initiating operation of surgical instrument 10, if the instrument is shipped with the anvil and cartridge assemblies unattached to the instrument, the clinician assembles end effector 16 by attaching center rod 38 to rod 90 as described above. In alternate embodiments, the instrument can be packaged fully assembled with the rod 90 attached to the center rod 38. In other embodiments, the center rod 38 with attached second cartridge 32, the first anvil assembly 34, and the second anvil assembly 36 are provided as separate components for attachment to the instrument. In such embodiments, the clinician would first slide first and second anvil assemblies 34, 36 onto central rod 38. (In the embodiment with detents, the clinician would slide the anvil assemblies onto the central rod 38 until the detent mechanisms discussed above engage and provide a tactile feel to the clinician that they are in place).

Once end effector 16 is assembled, the clinician can clamp tissue, cut, and/or join tissue. In one exemplary embodiment, end effector 16 is inserted inside a tubular organ "O", such as a bowel, through the patient's anus until end effector 16 reaches an area adjacent to the tumor or desired surgical site.

Figure 7:
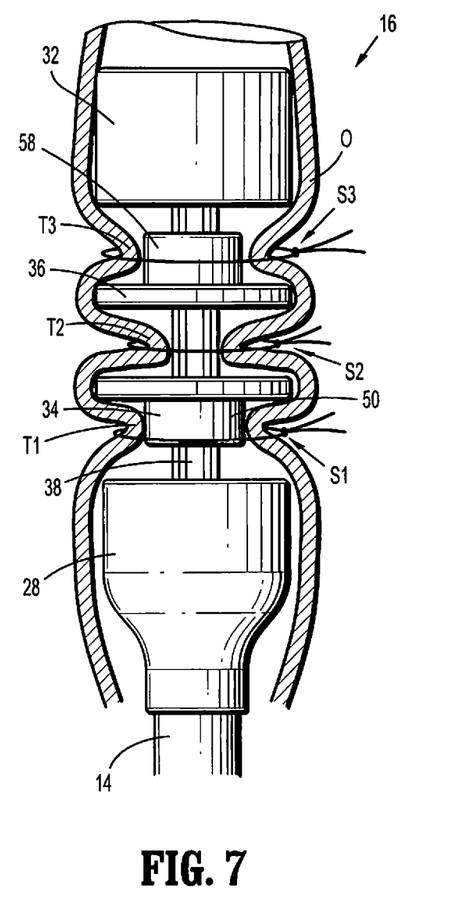
FIG. 7 is a longitudinal view of the end effector of the surgical instrument shown in FIG. 1 positioned inside a body organ and showing sutures surrounding portions of the body organ.
Figure 9:
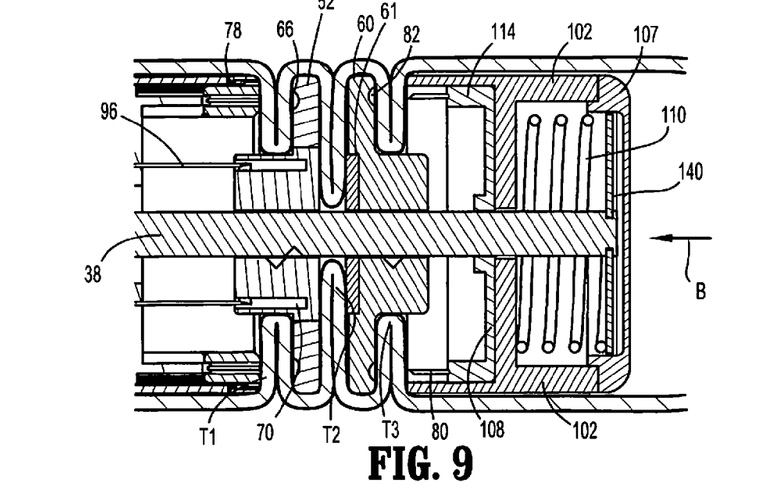
FIG. 9 is a longitudinal cross-sectional view of a distal portion of the surgical instrument shown in FIG. 1, depicting the stage of operation of FIG. 8.

As seen in FIGS. 7 and 9, to clamp tissue, the clinician first places end effector 16 adjacent to tissue such that a first tissue portion T1 is positioned between first cartridge assembly 28 and first anvil assembly 34, a second tissue portion T2 is positioned between first anvil assembly 34 and second anvil assembly 36, and a third tissue portion T3 is positioned between second anvil assembly 36 and second cartridge assembly 32. Subsequently, the clinician wraps three purse string sutures S1, S2, S3 around tubular organ "O" and tightens sutures S1, S2, S3 to draw portions of tubular organ "O" closer to central rod 38. Specifically, one suture S1 is wrapped and tightened around tissue portion T1, which is located between the first cartridge assembly 28 and first anvil assembly 34, another suture S2 is wrapped and tightened around tissue portion T2, which is located between first anvil assembly 34 and second anvil assembly 36, and yet a further suture S3 is wrapped and tightened around tissue portion T3, which is located between second anvil assembly 36 and second cartridge assembly 32. As shown, tissue portion T1 is tightened against tubular portion 50 of first anvil assembly 34, tissue portion T2 is tightened against central rod 38 and third tissue portion T3 is tightened against tubular portion 58 of second anvil assembly 36.

Figure 8:
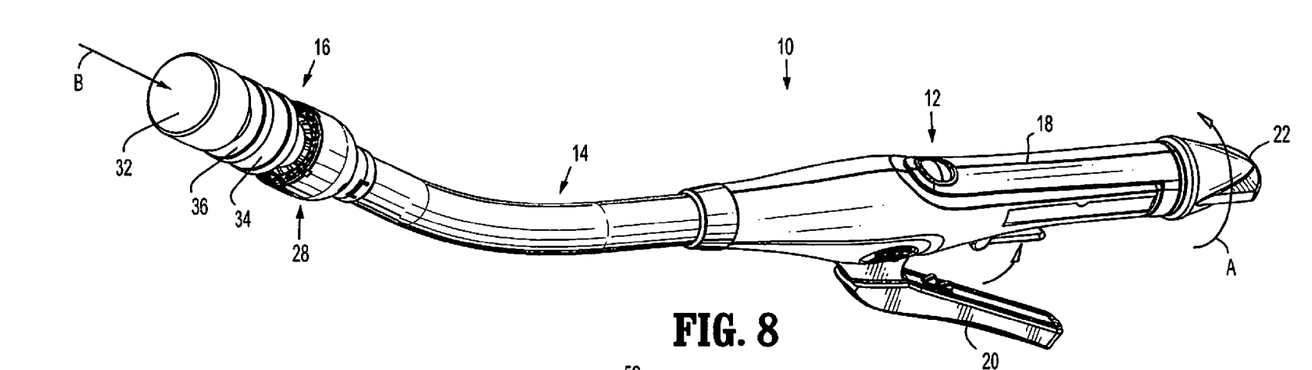
FIG. 8 is a perspective view of the surgical instrument shown in FIG. 1 in a first stage of operation of said surgical instrument.

Thereafter, the clinician rotates approximation knob 22 relative to stationary handle 18 in the direction indicated by arrow "A" (see FIG. 8), for example, to move end effector 16 from an open position (FIG. 6) to an approximated position (FIGS. 8 and 9). That is, in response to this rotation, central rod 38 moves proximally (due to its operative connection to rod 90 and approximation link assembly 88) and therefore urges second cartridge assembly 32, first anvil assembly 34, and second anvil 36 assembly in a proximal direction as indicated by arrow "B" to clamp the tissue portions T1, T2, T3 (See FIGS. 8 and 9). Note that as the central rod is approximated, the anvil assemblies can slide along central rod to clamp tissue. As central rod 38 moves proximally in the direction indicated by arrows "B," so does attached cartridge housing 102 and after sufficient movement eventually starts to compress tissue between second cartridge 32 and second anvil 36. At some point, resistance of clamped tissue becomes so great that it stops movement of cartridge housing 102 with respect to second anvil 36 and starts movement with respect to center rod 38. Relative motion between center rod 38 and cartridge housing 102 is possible due to elastic properties of biasing member 110.

Figure 10:
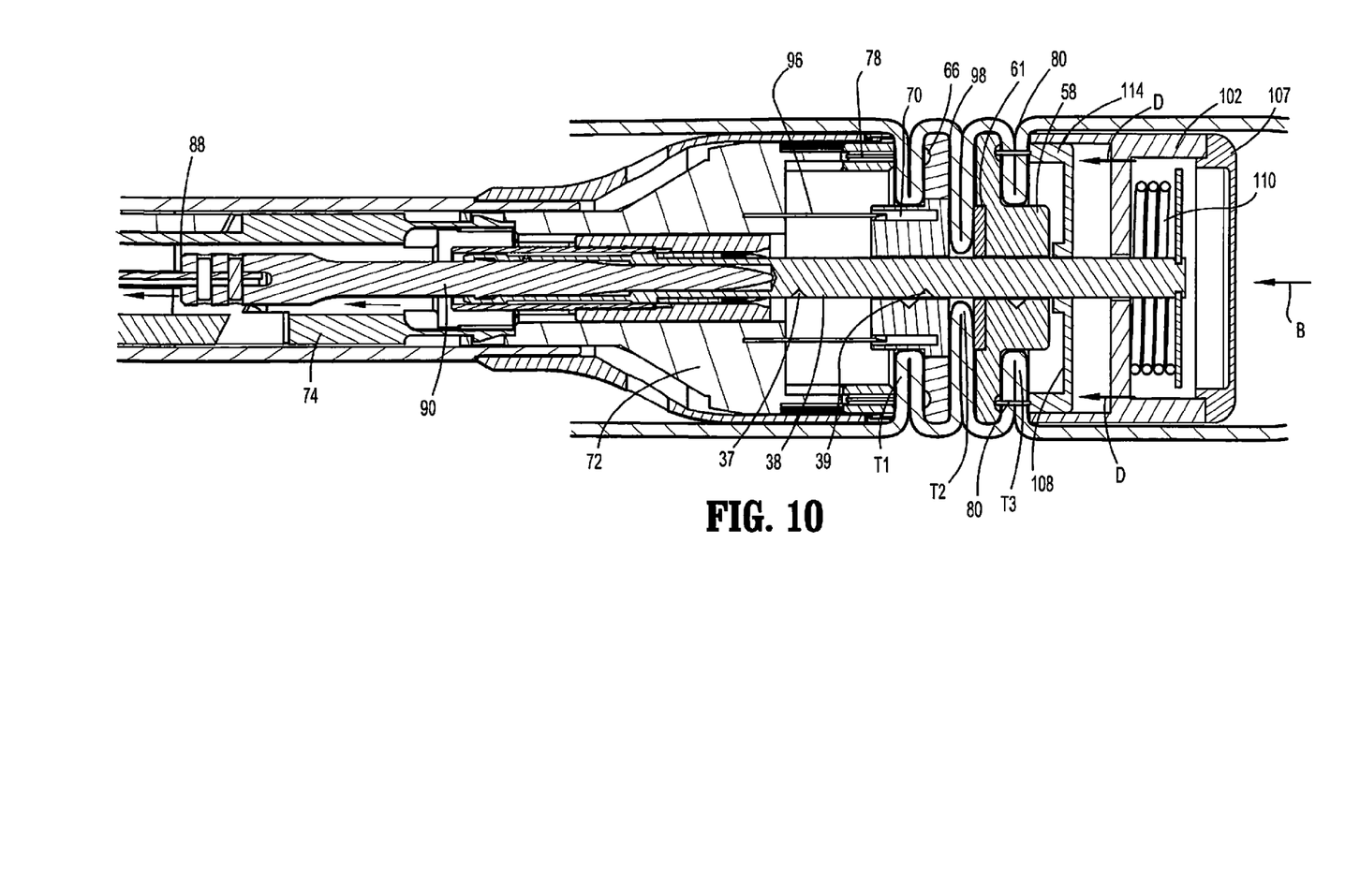
FIG. 10 is a longitudinal cross-sectional view of an anvil assembly and a cartridge assembly of the surgical instrument shown in FIG. 1 during a further stage of operation.

After clamping and compression of tissue between second cartridge 32 and second anvil 36, center rod 38 with attached fastener pusher 108 approximates further in the direction indicated by arrows "D" (FIG. 10) driving fingers 114 proximally into slots 112. Fingers 114 then push fasteners 80 out of second cartridge assembly 32 (into contact with pockets 82) to fasten the third tissue portion T3 (FIG. 10) clamped between second cartridge assembly 32 and second anvil assembly 36. Thus, as can be appreciated, the fasteners 80 are fired after the anvil assembly 36 and second cartridge assembly 32 are approximated. By firing the fasteners, a peripheral portion of the organ is clamped as can be seen in FIG. 10 which reduces leakage by limiting flow.

Figure 11:
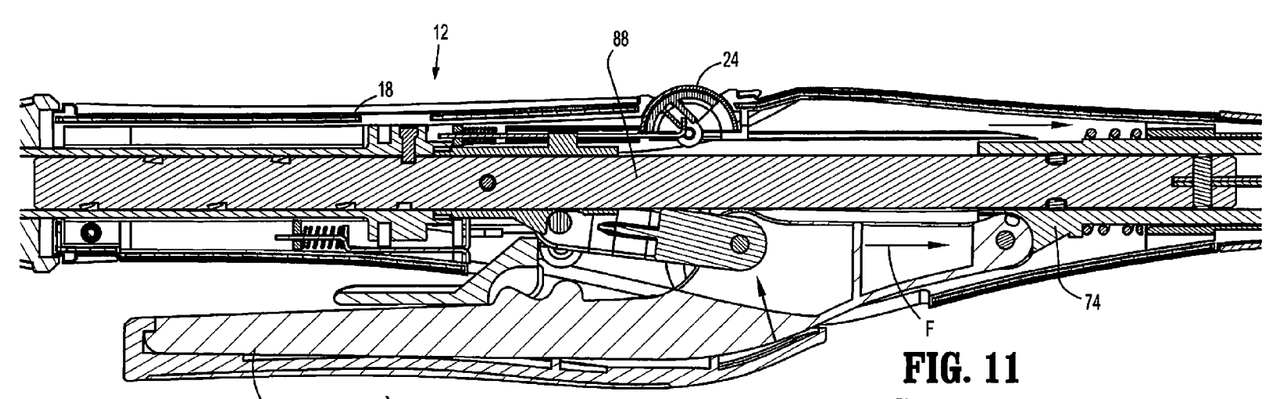
FIG. 11 is a longitudinal cross-sectional view of the handle assembly of the surgical instrument of FIG. 1 in the approximated or fired position.
Figure 12:
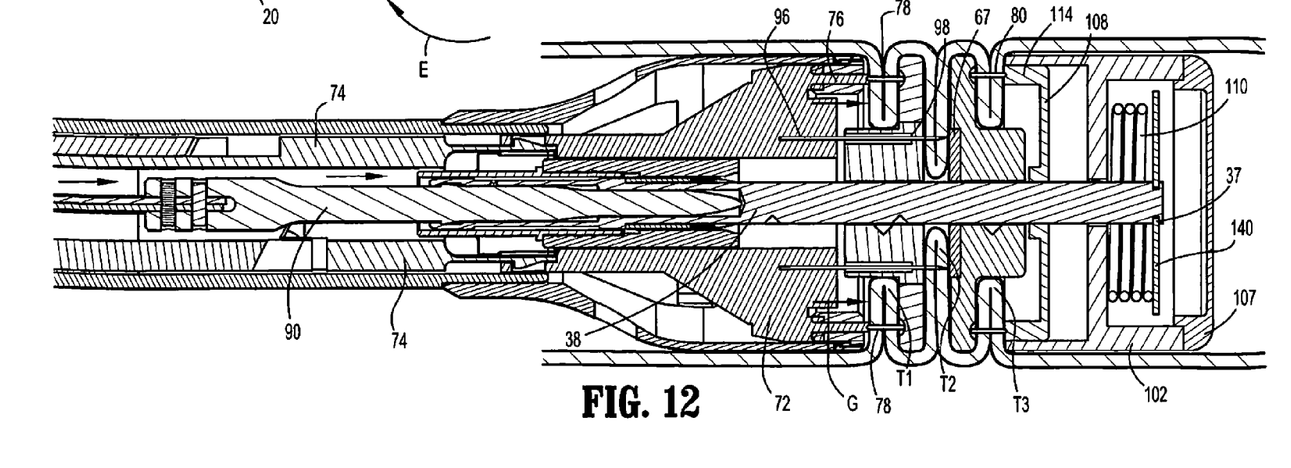
FIG. 12 is a longitudinal cross-sectional view of the end effector corresponding to the position of the handle assembly of FIG. 11.
Figure 13:
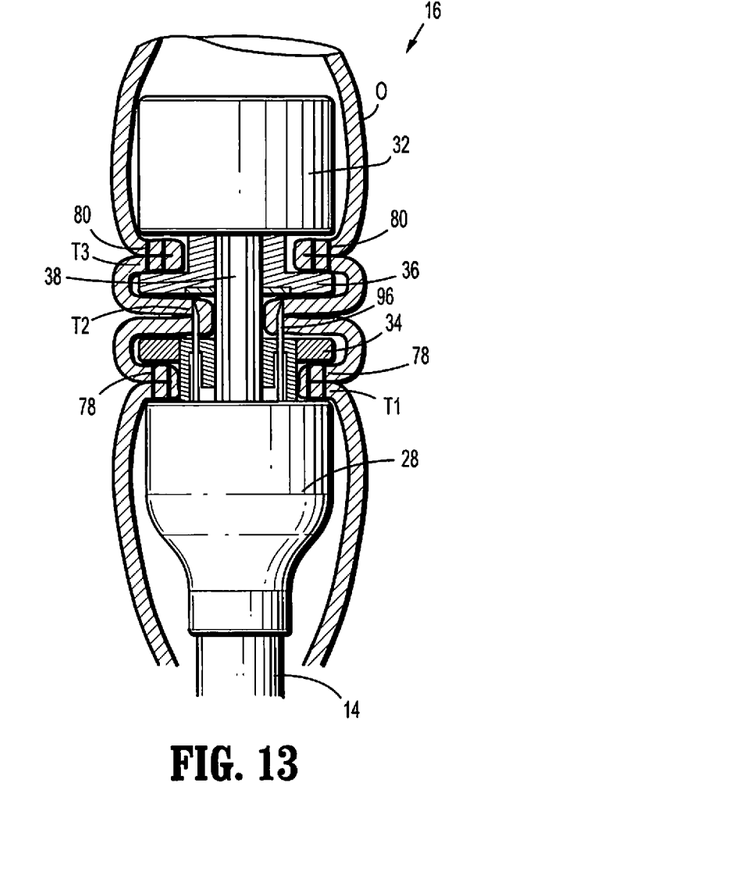
FIG. 13 is a longitudinal view similar to FIG. 7 showing the end effector inside a body organ after approximation and actuation.
Figure 14:
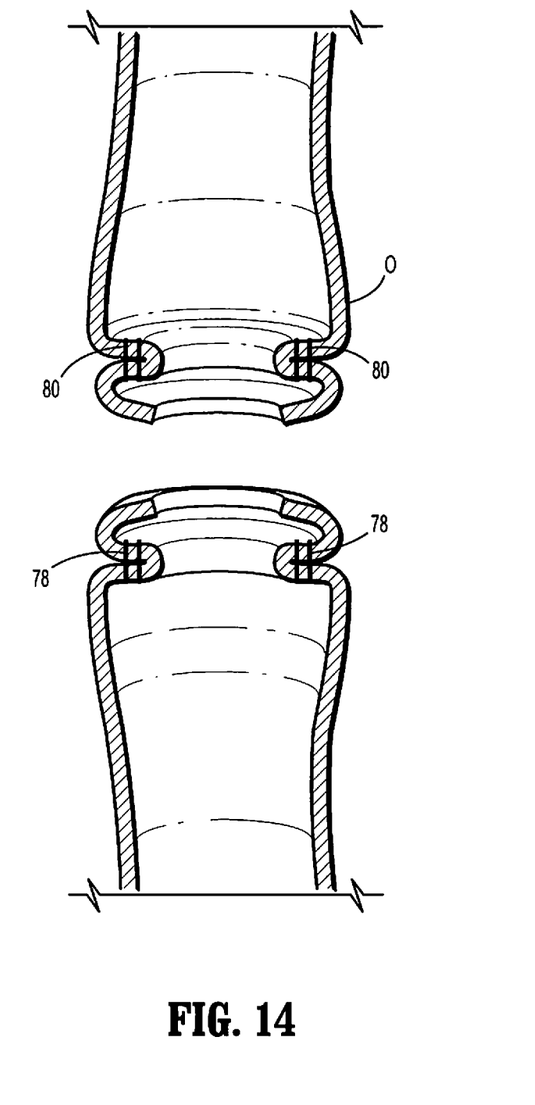
FIG. 14 is a longitudinal view of the body organ shown in FIG. 13 after cutting and fastening of the body organ with the surgical instrument of FIG. 1 and removal of the instrument.

To eject fasteners 78 housed in first cartridge assembly 32, the clinician actuates handle assembly 12 by moving firing trigger 20 toward stationary handle 18 in the direction indicated by arrow "E" (FIG. 11). Upon actuation of handle assembly 12, firing link assembly 74 translates distally in the direction indicated by arrow "F" (FIG. 11). In response to the distal translation of firing link assembly 74, fastener pusher 72 moves distally in the direction indicated by arrow "G," (FIG. 12) driving fingers 76 into slots 68. Consequently, fingers 76 push fasteners 78 out of first cartridge assembly 28 to fasten the first tissue portion T1 (FIG. 12) located between first cartridge assembly 28 and first anvil assembly 34. The distal movement of fastener pusher 72 also causes knife 96 to move distally toward first anvil assembly 34. As a consequence, knife 96 travels through annular space 70 of first anvil assembly 34 and then breaks through breakable annular portion 98 to reach proximal surface 100 of tubular portion 58 (see FIG. 12) where it becomes embedded in cut ring 61. During this distal translation, knife 96 cuts the second tissue portion T2 located between first anvil assembly 34 and second anvil assembly 36. The clinician then moves end effector 16 back toward the open position by rotating knob 22 in the opposite direction, thereby moving approximation link assembly 88 in a distal direction to move the first and second anvil assemblies 34, 36 and the second cartridge assembly 32 distally. The surgeon then removes the surgical instrument 10 from tubular organ "O" (FIG. 14).

Thereafter, a circular anastomosis instrument can be inserted through the lower tissue portion and into the tubular organ O. The instrument is clamped to approximate the two portions (since a tissue portion in between has been removed) and then staples are fired to join the portions.

Thus, as can be appreciated, one use of the instrument is in a lower anterior resection procedure. Clamping of the tissue organ O above the intended resection area enables wash out (cleaning out) of the area below the clamping, with stapling occurring below the clamping. This is achieved with access through the anus of the patient.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

What is claimed is:

1. An end effector for use with a surgical instrument, comprising:
   a first cartridge assembly configured to deploy a first set of fasteners;
   a second cartridge assembly, a proximal-most portion of the second cartridge assembly being disposed distally of a distal-most portion of the first cartridge assembly, wherein the second cartridge assembly is configured to move between an open position and an approximated position to clamp tissue; and
   a central rod having a longitudinal axis and extending between the first cartridge assembly and the second cartridge assembly, the central rod movable longitudinally to move the second cartridge assembly between the open and approximated positions, the second cartridge assembly being slidably positioned on the central rod.

2. The end effector of claim 1, further comprising a first anvil assembly disposed distally of the first cartridge assembly.

3. The end effector of claim 2, further comprising a second anvil assembly disposed distally of the first anvil assembly.

4. The end effector of claim 3, wherein the second cartridge assembly is configured to deploy a second set of fasteners once the second cartridge assembly has moved to the approximated position.

5. The end effector of claim 3, wherein each of the first anvil assembly and the second anvil assembly is mounted on the central rod for movement in response to movement of the central rod.

6. The end effector of claim 4, wherein the second cartridge assembly includes a fastener pusher adapted to move between a distal position and a proximal position to eject the second set of fasteners from the second cartridge assembly.

7. The end effector of claim 6, wherein the fastener pusher of the second cartridge assembly is operatively connected to the central rod.

8. The end effector of claim 7, wherein the second cartridge assembly further comprises a biasing member, wherein the biasing member biases a cartridge housing against the fastener pusher.

9. The end effector of claim 3, wherein the first cartridge assembly further comprises a knife movable between a proximal position and a distal position.

10. The end effector of claim 9, wherein the first anvil assembly includes a weakened portion that is configured to break when the knife moves therethrough.

11. The end effector of claim 1, wherein the end effector is removably mountable to a surgical instrument.

12. The end effector of claim 2, where the first anvil assembly comprises a plurality of anvil pockets arranged in a substantially annular array and configured to deform the first set of fasteners, the first set of fasteners arranged in a substantially annular array.

13. The end effector of claim 4, wherein the central rod is removably mounted to a rod of the surgical instrument and the central rod is slidable to approximate the anvil assemblies and fastener cartridge assemblies.

14. An end effector for use with a surgical instrument, comprising:
   a first cartridge assembly configured to deploy a first set of fasteners;
   a second cartridge assembly disposed distally of the first cartridge assembly, wherein the second cartridge assembly is configured to move between an open position and an approximated position to clamp tissue; and
   a central rod having a longitudinal axis and extending between the first cartridge assembly and the second cartridge assembly, the central rod movable longitudinally to move the second cartridge assembly between the open and approximated positions, wherein the longitudinal axis extends through the first cartridge assembly and the second cartridge assembly when the second cartridge assembly is in the open position.

15. A surgical instrument for joining tissue, comprising:
   a handle assembly;
   an elongated portion extending distally from the handle assembly and defining a longitudinal axis, the elongated portion having a proximal portion and a distal portion;
   an end effector disposed adjacent the distal portion of the elongated portion, the end effector including:
   a first cartridge assembly configured to deploy a first set of fasteners, the first cartridge assembly being positioned substantially along the longitudinal axis; and
   a second cartridge assembly disposed distally of the first cartridge assembly, the second cartridge assembly being positioned substantially along the longitudinal axis.

16. The surgical instrument of claim 15, further comprising a central rod extending between the first cartridge assembly and the second cartridge assembly the central rod movable substantially along the longitudinal axis to move the second cartridge assembly along the longitudinal axis.

17. The end effector of claim 1, wherein radial centers of the first cartridge assembly and the second cartridge assembly are aligned with the longitudinal axis when the second cartridge assembly is in its open position and its approximated position.

18. The end effector of claim 14, wherein radial centers of the first cartridge assembly and the second cartridge assembly are aligned with the longitudinal axis when the second cartridge assembly is in its open position and its approximated position.

19. The surgical instrument of claim 15, wherein radial centers of the first cartridge assembly and the second cartridge assembly are aligned with the longitudinal axis when the second cartridge assembly is in its open position and its approximated position.

20. The end effector of claim 1, wherein the second cartridge is solely movable along the longitudinal axis with respect to the first cartridge assembly.

21. The end effector of claim 14, wherein the second cartridge is solely movable along the longitudinal axis with respect to the first cartridge assembly.

22. The surgical instrument of claim 15, wherein the second cartridge is solely movable along the longitudinal axis with respect to the first cartridge assembly.

23. The end effector of claim 1, wherein the entirety of the second cartridge is distally disposed of the entirety of the first cartridge when the second cartridge is in both the open an approximated positions.

24. The end effector of claim 14, wherein the entirety of the second cartridge is distally disposed of the entirety of the first cartridge when the second cartridge is in both the open an approximated positions.

25. The surgical instrument of claim 15, wherein the entirety of the second cartridge is distally disposed of the entirety of the first cartridge when the second cartridge is in both the open an approximated positions.

* * * * *